United States Patent
Field

(10) Patent No.: US 8,398,596 B2
(45) Date of Patent: Mar. 19, 2013

(54) NEEDLE ASSEMBLIES AND METHODS

(75) Inventor: Stephen James Field, Canterbury (GB)

(73) Assignee: Smiths Group PLC, London (GB)

( * ) Notice: Subject to any disclaimer, the term of this patent is extended or adjusted under 35 U.S.C. 154(b) by 243 days.

(21) Appl. No.: 12/734,187

(22) PCT Filed: Oct. 24, 2008

(86) PCT No.: PCT/GB2008/003599
§ 371 (c)(1),
(2), (4) Date: Apr. 16, 2010

(87) PCT Pub. No.: WO2009/063166
PCT Pub. Date: May 22, 2009

(65) Prior Publication Data
US 2010/0256577 A1    Oct. 7, 2010

(30) Foreign Application Priority Data
Nov. 15, 2007   (GB) .................................. 0722406.6

(51) Int. Cl.
*A61M 5/178*   (2006.01)
(52) U.S. Cl. ..................... 604/164.05; 604/264; 604/272
(58) Field of Classification Search .................. 604/264, 604/272, 164.01, 164.05, 164.08
See application file for complete search history.

(56) References Cited

U.S. PATENT DOCUMENTS

| | | | |
|---|---|---|---|
| 4,582,061 A | 4/1986 | Fry | |
| 5,383,466 A * | 1/1995 | Partika | 600/459 |
| 6,018,676 A | 1/2000 | Davis et al. | |
| 6,280,399 B1 * | 8/2001 | Rossin et al. | 600/567 |
| 2004/0193055 A1 * | 9/2004 | Field et al. | 600/458 |
| 2004/0236212 A1 | 11/2004 | Jones et al. | |
| 2005/0165342 A1 * | 7/2005 | Odland | 604/5.01 |
| 2008/0058702 A1 | 3/2008 | Arndt et al. | |

FOREIGN PATENT DOCUMENTS

| | | |
|---|---|---|
| DE | 102 40 279 | 4/2003 |
| DE | 102006051978 | 5/2008 |
| EP | 0 386 936 | 9/1990 |
| JP | 2004-248713 | 9/2004 |
| WO | 98/22022 | 5/1998 |

OTHER PUBLICATIONS

PCT International Preliminary Report on Patentability, issued May 18, 2010, (7 sheets).

* cited by examiner

*Primary Examiner* — Laura Bouchelle
(74) *Attorney, Agent, or Firm* — Louis Woo

(57) ABSTRACT

A needle assembly comprises a metal needle (1) with a hub (13) and a marker in the form of a bubble-filled plastics rod (2) inserted within the needle. The rod (2) makes the assembly more visible under ultrasound observation when confirming correct placement of the needle (1) and is subsequently removed when correct placement has been confirmed.

6 Claims, 1 Drawing Sheet

NEEDLE ASSEMBLIES AND METHODS

This invention relates to needle assemblies of the kind including a hollow metal needle.

Ultrasound scanners are used increasingly to help direct or check placement of catheters and other devices inserted in the body. Some of these devices are not normally very visible under ultrasound because of their shape, size or the fact that the material from which they are made has similar reflectance acoustic impedance to the tissue or body fluid within which they are inserted. Attempts have been made to increase the visibility of medico-surgical devices under ultrasound observation in various ways. Where the device, such as a needle, is of a metal the usual way of increasing its visibility is by modifying its surface, such as by forming grooves or indentations in its surface. A reflective coating may be applied to the device, such as incorporating bubbles, as described in WO98/19713 and EP0624342. Where the device is of a plastics material, such as a catheter of the kind described in GB2379610 the wall may include gas bubbles or a bubble-containing material may be incorporated in a stripe occupying only a part of the circumference. GB2400804 describes a similar catheter with several layers. U.S. Pat. No. 7,258,669 describes a catheter with a helical, gas-filled lumen extending along its length. DE 102006051978 describes a bubble-filled rod inserted along the bore of a flexible plastics catheter to enhance visibility under ultrasound observation. The ultrasound visibility of a catheter in a body can also be enhanced by supplying a fluid containing bubbles along the bore of the catheter. These arrangements, however, are not suitable in all cases. It may, for example, be undesirable to coat a device because of the risk of detachment. Also, some arrangements do not provide visibility along the length of the device. Altering the surface of a metal device by forming grooves or the like may reduce the smoothness of the device. Gas bubbles can be used in many applications but with small diameter catheters, the bubbles could alter the physical characteristics of the catheter.

It is an object of the present invention to provide an alternative needle assembly and a method of its use.

According to one aspect of the present invention there is provided a needle assembly of the above-specified kind, characterised in that the assembly includes a marker removably mounted with the needle and containing at least one closed gas interstice such that the marker is visible under ultrasound observation and such that the ultrasound visibility of the assembly with the marker is greater than that of the needle alone.

The marker is preferably of a plastics material. The at least one gas interstice is preferably provided by a plurality of gas bubbles within the thickness of the marker. The gas interstice or interstices preferably extend along substantially the entire length of the marker but could be confined to one or more localised regions. The marker is preferably in the form of a stylet removably inserted within a bore of the needle.

According to another aspect of the present invention there is provided a marker for use with a needle assembly according to the above one aspect of the present invention.

According to a further aspect of the present invention there is provided a method of confirming correct placement of a needle in a body, characterised in that the method includes the step of mounting a bubble-filled marker with the needle before or after placement, viewing the body in the location of the needle with an ultrasound instrument such that the marker increases the visibility of the combination of the needle and marker compared with the needle alone, and subsequently removing the marker to leave the needle in position.

The bubble-filled marker is preferably a rod inserted within a bore of the needle and subsequently removed from the bore to allow passage of fluid along the bore.

A needle assembly and its method of use, according to the present invention, will now be described, by way of example, with reference to the accompanying drawings, in which.

Figure 1:
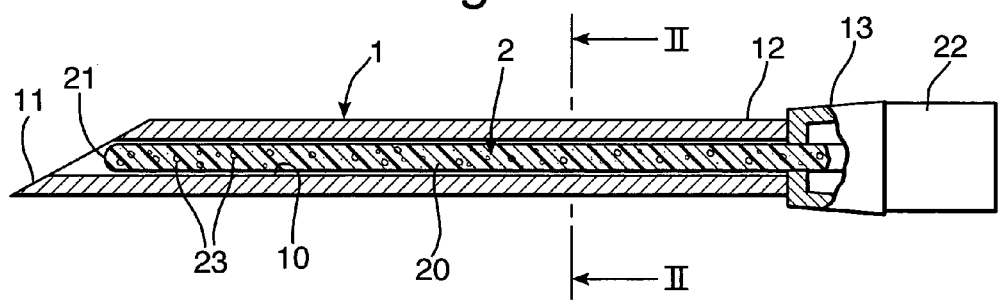
FIG. 1 is a cross-sectional side elevation view of the assembly to an enlarged scale.
Figure 2:
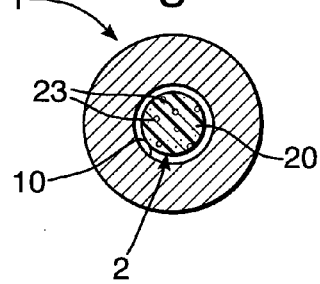
FIG. 2 is an enlarged transverse sectional view along the line II-II of FIG. 1.

The needle 1 has a smooth external surface with a circular section and a coaxial bore 10 extending along its length. At its forward, patient end 11 the needle is bevelled to provide a sharp, penetrating tip. At its rear, machine end 12 the needle has a conventional hub 13 by which the needle can be attached to an external device such as the nose of a syringe or the like. The external diameter of the needle 1 is typically 0.5-2 mm and its length is typically 50-150 mm. The smooth surface of the needle 1 is such that it is not very visible by itself under ultrasound observation. Although the needle is shown as having an open tip, it could be closed at its end and have a side opening close to its tip.

The stylet 2 comprises a solid, cylindrical rod 20 with a rounded forward or patient end 21 and is attached to a handle 22 at its rear end. The external diameter of the rod 20 is such that it is a free sliding fit within the bore 10 of the needle 1 and, when its handle 22 abuts the rear end of the hub 13, the patient end 21 lies substantially level with the patient end 11 of the needle. The rod 20 is extruded from a flexible plastics material, such as PEBA, nylon, PVC, polyethylene, polypropylene, polyester or polyurethane to which a foaming agent has been added so that the rod is filled with gas interstices in the form of bubbles 23 along its entire length. The size and density of the bubbles 23 are selected to ensure that the stylet 2 is highly echogenic. Typically the gas bubbles 23 have a size in the range $0.1\mu$ to $300\mu$, preferably having a size in the range $1\mu$ to $50\mu$ and most preferably having a size in the range $5\mu$ to $10\mu$. It will be appreciated that there are other ways of forming gas interstices such as by including gas-filled polymer or glass microparticles into the plastics material. The gas within the bubbles or interstices could be of any kind and could be a vacuum. Instead of having a multiplicity of gas bubbles, a single gas interstice could be provided by means of a hollow bore extending along the stylet and closed at both ends. The external surface of the stylet 2 could be coated with a lubricant or a lubricious or low friction layer to make it easier to insert and remove from the needle 1. The stylet 2 could instead be rigid, such as of ABS or styrenic materials. If the needle were not straight, the stylet would be preferably flexible. The stylet may have a round cross section but could be of other shapes.

Figure 3:
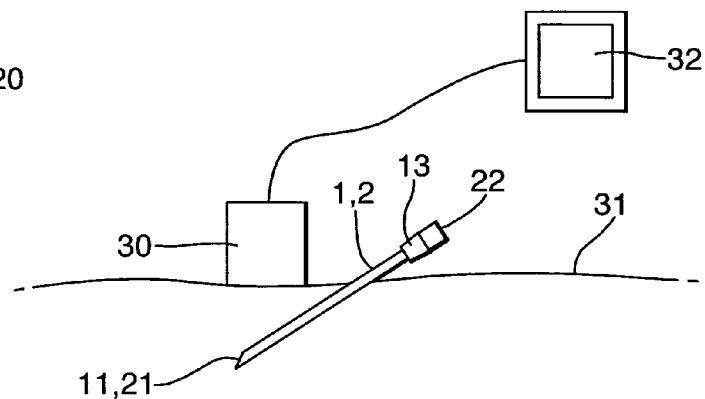
FIG. 3 illustrates the assembly in use.

The stylet 2 can be used in several different ways. For example, the stylet 2 could be inserted in the needle 1 prior to insertion of the needle into the body so that the entire assembly of the needle and stylet is inserted at the same time. The scanning head 30 of an ultrasound instrument is then held against the skin 31 and the image of the underlying structure is viewed on a screen 32 of the instrument, as shown in FIG. 3. The stylet 2 makes the assembly highly reflective of ultrasound energy so the location of the assembly along its entire length is clearly visible on the screen 32. The clinician can then reposition the assembly as necessary until its tip 11, 21 or some other desired part of the needle (such as an eye) is in the desired position. Then he pulls out the stylet 2 to leave the needle 1 in position so that fluid can be flowed along the bore 10 of the needle, such as medication for administration to the patient or a sample taken from the patient via the needle.

Alternatively, a needle could be inserted into the body without the echogenic stylet in position. When the needle is positioned at what is thought to be the correct position, the clinician would insert the echogenic stylet so that the correct positioning of the needle could then be confirmed by observation using the ultrasound scanner.

The stylet need not be a solid rod, as described, but could have an open or closed bore extending along its length or a wire or other member to alter its characteristics. Although it is generally preferable for the bubbles or other gas interstices to be provided along the entire length of the stylet, this is not essential and they could, instead, just be provided along a part of the length, such as towards the patient end.

Although the removable marker is preferably of a bubble-filled plastics, it could be of other materials, such as a sintered metal having gas interstices. The region of the marker with the bubbles or other gas interstices need not extend along the entire length of the marker but could be provided in one or more localised regions, for example, they could be in short lengths spaced at regular intervals along the marker to assist in distance measuring.

Figure 4:
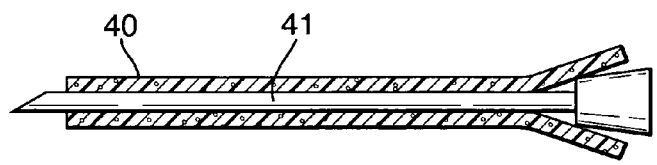
FIG. 4 is a cross-sectional side elevation view of the forward end of an alternative assembly With reference first to FIGS. 1 to 3, the assembly comprises a conventional rigid, metal needle or cannula 1 and a novel ultrasound marker in the form of a stylet 2 inserted within it.

The ultrasound marker need not be a stylet inserted within a needle but could instead be an ultrasound-visible sheath or sleeve 40 extended along the outside of the needle, such as shown in FIG. 4. By slipping the echogenic sheath 40 along the outside of the needle 41, the combined assembly of the needle and sheath can be observed more clearly on an ultrasound scanner. When the needle 41 has been positioned correctly, the sheath 40 is slipped off to leave the needle in position. The sheath 40 preferably has a tear line to enable it to be split into two parts so that it can clear the needle hub.

It will be appreciated that the present invention is not confined to visual ultrasound observation since it could have advantages when used with an ultrasound scanner that provides, for example an audible feedback to the user, such as an increasing tone when positioned in alignment with an ultrasound reflective device.

The invention claimed is:

1. A needle assembly including a hollow metal needle, characterized in that the assembly includes a plastic sleeve removably mounted along the outside of the needle and containing a plurality of gas bubbles within the thickness of the sleeve such that the sleeve is visible under ultrasound observation and such that the ultrasound visibility of the assembly with the sleeve is greater than that of the needle alone.

2. An assembly according to claim 1, characterized in that the gas bubbles extend along substantially the entire length of the marker.

3. An assembly according to claim 1, characterized in that the gas bubbles extend along one or more localized regions of the marker.

4. An assembly according to claim 1, characterized in that the sleeve can be split along its length to enable removal from the rear end of the needle.

5. A method of confirming correct placement of a metal needle in a body, characterized in that the method includes the steps of mounting a bubble-filled sleeve along the outside of the needle before or after placement, viewing the body in the location of the needle with an ultrasound instrument such that the sleeve increases the visibility of the combination of the needle and sleeve compared with the needle alone, and subsequently removing the sleeve to leave the needle in position.

6. A method according to claim 5, characterized in that the sleeve is subsequently removed from the needle by splitting the sleeve along its length.

* * * * *